United States Patent
Wu et al.

(10) Patent No.: US 7,626,016 B2
(45) Date of Patent: Dec. 1, 2009

(54) PROCESS FOR PREPARING SUCROSE-6-ESTER

(75) Inventors: Jun Jing Wu, Shijiazhuang (CN); Guang Li Wu, Shijiazhuang (CN); Qing Hai Cai, Shijiazhuang (CN); Shou Xinyu, Shijiazhuang (CN); Zi Wen Li, Shijiazhuang (CN); Shang Liu, Shijiazhuang (CN); Man Tang Wang, Shijiazhuang (CN)

(73) Assignee: Hebei Sukerui Science and Technology Co., Ltd. (CN)

( * ) Notice: Subject to any disclaimer, the term of this patent is extended or adjusted under 35 U.S.C. 154(b) by 126 days.

(21) Appl. No.: 11/841,435

(22) Filed: Aug. 20, 2007

(65) Prior Publication Data

US 2008/0058508 A1 Mar. 6, 2008

(30) Foreign Application Priority Data

Aug. 30, 2006 (CN) .................. 2006 1 0112057

(51) Int. Cl.
*C07H 1/00* (2006.01)
*C07H 3/04* (2006.01)
*C07H 13/02* (2006.01)
*C07H 5/02* (2006.01)

(52) U.S. Cl. .................. 536/124; 536/123.13; 536/115; 536/18.4; 536/122; 536/4.1

(58) Field of Classification Search ................. 536/124, 536/123.13, 115, 18.4, 122, 4.1
See application file for complete search history.

(56) References Cited

U.S. PATENT DOCUMENTS

| 4,262,115 A | 4/1981 | Khan et al. |
| 4,291,158 A | 9/1981 | Luteri |
| 4,324,888 A | 4/1982 | Rathbone |
| 4,345,933 A | 8/1982 | Luteri |
| 4,362,869 A | 12/1982 | Jenner et al. |
| 4,380,476 A | 4/1983 | Mufti et al. |
| 4,405,654 A | 9/1983 | Lee |
| 4,549,013 A | 10/1985 | Hough et al. |
| 4,612,373 A | 9/1986 | Khan et al. |
| 4,617,269 A | 10/1986 | Rathbone et al. |
| 4,980,463 A | 12/1990 | Walkup et al. |

FOREIGN PATENT DOCUMENTS

| CN | 1176094 C | 11/2004 |
| EP | 0260979 B1 | 5/1991 |
| GB | 2079749 A | 1/1982 |

OTHER PUBLICATIONS

John M. Ballard, et al., "Sucrochemistry. Part XII. Reaction of Sucrose with Sulphuryl Chloride", Feb. 22, 1973, J.C.S. Perkin I, pp. 1524-1528.

S. Hanessian and N. R. Plessas, "A New Synthesis of Chlorodeoxy-sugars" Sep. 14, 1967; Com. 985, Chemical Communications, The Chemical Society, London, pp. 1152-1155.

R. J. Ferrier, "Carbohydrate Chemistry Monosaccharides, Disaccharides, and Specific Oligosaccharides" (1990), pp. 177-191 The Royal Society of Chemistry.

Eilingsfeld, et al. "Amidchloride und Carbamidchloride", (1960), , pp. 836-845, Angewandte Chemie, 72 Jahrgang, No. 22.

Roy L. Whistler, et al., "Methods in Carbohydrate Chemistry", vol. VIII General Methods, pp. 227-231, (1980), Academic Press, Inc.

Roy L. Whistler, et al., "Methods in Carbohydrate Chemistry", vol. VI, General Carbohydrate Methods, pp. 190-193, (1972), Academic Press, Inc.

Stephen Hanessian, et al., "Reactions of Carbohydrates with (Halomethylene) dimethyliminium Halides and Related Reagents. Synthesis of Some Chlorodeoxy Sugars", vol. 34, No. 7, Jul. 1969, pp. 2163-2170, Dept. of Chemistry, University of Montreal and Research Laboratories, Ann Arbor, Michigan.

John L. Hickson, "Sucrochemistry" ACS Symposium Series 41, "Selective Substitution of Hydroxyl Groups in Sucrose" by Leslie Hough (1977) American Chemical Society, pp. 9-21.

Leslie Hough, et al. "The Preparation of 4,6-Dichloro-4,6-Dideoxy-$\alpha$-$_D$-Galactopyranosyl 6-Chloro-6-Deoxy-$\beta$-$_D$-Fructofuranside and the Conversion of Chlorinated Derivatives Into Anhydrides" May 1975, pp. 37-44, Elsevier Scientific Publishing Company, Amsterdam.

(Continued)

*Primary Examiner*—Patrick T Lewis
*Assistant Examiner*—Michael C Henry
(74) *Attorney, Agent, or Firm*—Fish & Richardson P.C.

(57) ABSTRACT

This invention relates to a method for preparing a sucrose-6-ester. The method includes (i) reacting sucrose with a N,N-dimethylcarboxamide dimethyl acetal in an inert aprotic solvent to form a cyclic acetal of formula (I):

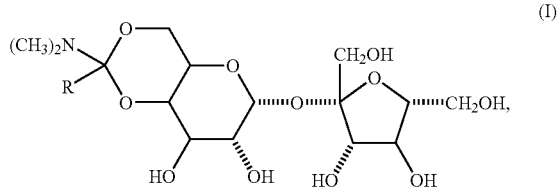

wherein R is $C_1$-$C_6$ alkyl, $C_3$-$C_{20}$ cycloalkyl, $C_1$-$C_{20}$ heterocycloalkyl, aryl, or heteroaryl; and (ii) subjecting the cyclic acetal to a mild acidic or neutral hydrolysis to provide a sucrose-6-ester of formula (II):

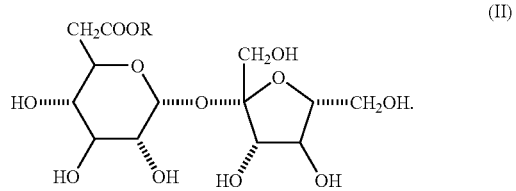

19 Claims, No Drawings

OTHER PUBLICATIONS

C. K. Lee, "Developments in Food Carbohydrate—2" M. R. Jenner "Sucrose" Chap. 2, pp. 91-143, (1980) Applied Science Publishers Ltd.

R. Stuart Tipson, Derek Horton "Advances in Carbohydrate Chemistry and Biochemisty", vol. 33, pp. 235-294 "The Chemistry of Sucrose" by Riaz Khan (1976) Academic Press.

Riaz Khan "Some Fundamental Aspects of the Chemistry of Sucrose" Fundamental Aspects, pp. 40-61, ACS Symposium (1977).

Melvin S. Newman and P. K. Sujeeth "Conversion of Aromatic and a,B-Unsaturated Aldehydes to Dichlorides by Thionyl Chlorida and Dimethylformamide" J. Org. Chem., vol. 43, No. 22, pp. 4367-4369 (1978) American Chemical Society.

R. Stuart Tipson, Derek Horton "Advances in Carbohydrate Chemisty and Biochemisty", vol. 28, pp. 225-306 "Deoxyhalogeno Sugars" by Walter A. Szarek (1973) Academic Press.

Heinz Günter Viehe and Zdenek Janousek "The Chemistry of Dichloromethylenammonium Salts", Angew. Chem Internat. Edit./ vol. 12, (1973) / No. 10, pp. 806-818.

PROCESS FOR PREPARING SUCROSE-6-ESTER

CROSS REFERENCE TO RELATED APPLICATION

Pursuant to 35 USC § 119, this application claims priority to Chinese Application No. 200610112057.6, filed Aug. 30, 2006, the contents of which are incorporated herein by reference.

BACKGROUND

Sucralose is a high intensity sweetener which is substantially calorie-free for human consumers. It is stable and safe to use. Three major methods are currently being used in synthesizing sucralose: (1) the raffinose method, (2) the all-hydroxyl protection method; and (3) the monoesterification method. In the first method, raffinose is sequentially chlorinated by thionyl chloride in the presence of triphenyl phosphine oxide and hydrolyzed by an enzyme to give sucralose. In the second method, the three primary hydroxyl groups in sucrose are first protected with trityl chloride. The protected compound is then acylated by acetate anhydride to obtain 6,1',6'-tri-O-tritylsucrose pentacetate, which is ultimately transformed to sucralose by sequential detritylation, transportation of acetyl group, chlorination, and deacylation. The third method is also called 6-hydroxyl protection method. In this method, the most active 6-hydroxyl group in sucrose is first protected by using a suitable protecting agent. The protected compound is then chlorinated and deprotected to form sucralose. There remains a need to develop a new method of preparing sucralose in high yield and purity at a low cost.

SUMMARY

In one aspect, this invention features a method for preparing a sucrose-6-ester. The method includes (i) reacting sucrose with a N,N-dimethylcarboxamide dimethyl acetal in an inert aprotic solvent to form a cyclic acetal of formula (I):

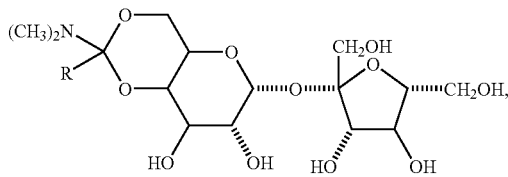

(I)

in which R is $C_1$-$C_6$ alkyl (e.g., methyl or ethyl), $C_3$-$C_{20}$ cycloalkyl, $C_1$-$C_{20}$ heterocycloalkyl, aryl (e.g., phenyl), or heteroaryl; and (ii) subjecting the cyclic acetal to a mild acidic or substantially neutral hydrolysis (e.g., at a pH within the range of from about 4 to about 7) to provide a sucrose-6-ester of formula (II):

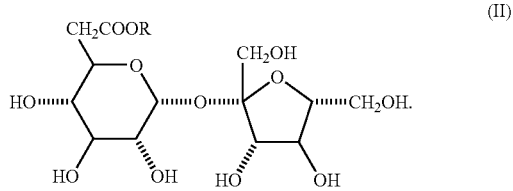

(II)

The amount of N,N-dimethylcarboxamide dimethyl acetal used in step (i) can be within the range of from about 0.9 to about 2.0 molar equivalents to the amount of sucrose. Examples of the N,N-dimethylcarboxamide dimethyl acetal include N,N-dimethylacetamide dimethyl acetal, N,N-dimethyl propionamide dimethyl acetal, and N,N-dimethylbenzamide dimethyl acetal. The inert aprotic solvent should not react under the relevant reaction conditions with other reagents (e.g., by means of an acidic proton) to a degree that interferes with the recovery of useful products. Examples of the inert aprotic solvent used in step (i) include N,N-dimethylformamide, dimethyl sulfoxide, N,N-dimethylacetamide, and pyridine. The reaction of step (i) can be carried out at a temperature within the range of from about 20° C. to about 90° C. for about 2 hours to about 6 hours.

The hydrolysis reaction in step (ii) can be carried out in an aqueous solution or a solution containing an organic solvent. When the hydrolysis is carried out in an aqueous solution, the amount of water in the aqueous solution can be within the range of from about 2 to about 10 molar equivalents of the amount of sucrose. Further, the hydrolysis can be carried out in the presence of an organic acid (e.g., acetic acid or formic acid), an inorganic acid (e.g., hydrochloric acid or sulfuric acid), or acidic ion exchange resin. Preferably, the hydrolysis can be carried out at a temperature not higher than about 20° C.

In another aspect, this invention features a compound of formula (I), in which R is $C_1$-$C_6$ alkyl (e.g., methyl or ethyl), $C_3$-$C_{20}$ cycloalkyl, $C_1$-$C_{20}$ heterocycloalkyl, aryl (e.g., phenyl), or heteroaryl.

In still another aspect, this invention features a method for preparing sucralose. The method includes (i) reacting sucrose with a N,N-dimethylcarboxamide dimethyl acetal in an inert aprotic solvent to form a cyclic acetal of formula (I), in which R is $C_1$-$C_6$ alkyl, $C_3$-$C_{20}$ cycloalkyl, $C_1$-$C_{20}$ heterocycloalkyl, aryl, or heteroaryl; (ii) subjecting the cyclic acetal to a mild acidic or neutral hydrolysis to provide a sucrose-6-ester of formula (II); (iii) treating the sucrose-6-ester with a chlorinating agent (e.g., a Vilsmeier agent such as N,N-dialkylchloroformiminium chloride) capable of effecting selective chlorination at the 4-, 1'-, 6'-positions to form a sucralose-6-ester; and (iv) treating the sucralose-6-ester with a base (e.g., sodium methylate) to obtain sucralose.

The details of one or more embodiments of the invention are set forth in the description below. Other features, objects, and advantages of the invention will be apparent from the description and from the claims.

DETAILED DESCRIPTION

This invention relates to an improved method of preparing sucrose-6-ester by using a novel sucrose derivative of formula (I) as a key intermediate. This method avoids complicated operations and can significantly reduce labor and equipment cost.

The method of this invention can be carried out as follows: An N,N-dimethylcarboxamide dimethyl acetal can first react with sucrose to form a cyclic acetal of formula (I), which can be readily converted to a sucrose-6-ester by neutral or mild acidic hydrolysis. The chemical formula of N,N-dimethylcarboxamide dimethyl acetal is $RC(OMe)_2NMe_2$, in which R can be $C_1$-$C_6$ alkyl (e.g., methyl or ethyl), $C_3$-$C_{20}$ cycloalkyl, $C_1$-$C_{20}$ heterocycloalkyl, aryl (e.g., phenyl), or heteroaryl. The reaction between the N,N-dimethylcarboxamide dimethyl acetal and sucrose to produce cyclic acetals is highly selective at the 6- and 4-hydroxyl groups. The cyclic acetal formation can be achieved quantitatively under suitable reactions conditions. The cyclic acetal thus obtained can be readily hydrolyzed at a neutral or mild acidic condition to give a sucrose-6-ester at a high yield without forming a side product sucrose-4-ester. By contrast, U.S. Pat. No. 4,889,928 discloses a method of preparing sucrose-6-ester via an alkyl orthoester intermediate with an additional step of converting a sucrose-4-ester to a sucrose-6-ester in the presence of a base. Thus, the method of this invention simplifies operation, produce good yields, and is suited to large-scale production.

The reaction between sucrose and N,N-dimethylcarboxamide dimethyl acetals is preferably carried out in a polar aprotic solvent, such as N,N-dimethylformamide and pyridine. The amount of solvent can range from three to ten times of that of sucrose. An insufficient amount of the solvent can hinder the reaction due to an increased concentration of sucrose, while an excessive amount of the solvent causes waste and inconvenience in post-treatment. The amount of the N,N-dimethylcarboxamide dimethyl acetal can be about 0.9 to about 2.0 molar equivalents to that of sucrose. In the hydrolysis reaction of the cyclic acetal, the water added is preferably from about 2 to about 10 molar equivalents of that of sucrose. The pH of the reaction mixture can be adjusted by using an organic acid, an inorganic acid, or acidic ion exchange resin. The hydrolysis reaction is preferably carried out at not higher than about 20° for about 10 minutes to about 60 minutes.

This invention also features a method of preparing sucralose. For example, sucrose can first be dissolved or suspended in a polar aprotic solvent. After N,N-dimethylcarboxamide dimethyl acetal is added (preferably dropwise and at a low speed), the mixture can be stirred at a suitable temperature (e.g., from about 20° C. to about 90° C.) for a certain period of time (e.g., from about 2 hours to about 6 hours) and then cooled below a suitable temperature (e.g., about 20° C.). Appropriate amounts of water or an acid can then be added to the mixture to adjust the pH (e.g., from about 4 to about 7). The mixture can be stirred for another suitable period of time to afford sucrose-6-ester of formula (II), which can be used in the next step either in a purified form or without further purification. Specifically, sucrose-6-esters can be chlorinated by a known chlorinating agent, such as a Vilsmeier agent, to give a sucralose-6-ester. A Vilsmeier agent can be prepared by reacting a tertiary amide (e.g., DMF) with an acid chloride (e.g., phosgene, thionyl chloride, or phosphorus chloride oxide). The chlorination reaction can be carried out by methods known in the art, such as those described in U.S. Pat. Nos. 4,980,463, 4,362,869, and 4,980,463, the contents of which are incorporated herein by reference in their entirety. The ester can then be deacylated in a base (e.g., a methanol and sodium methylate mixture) to afford the target compound sucralose.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

Synthesis of sucrose-6-acetate

A four-neck, round-bottom flask with stirring apparatus was charged with 34.2 g of sucrose and 140 mL of N,N-dimethylformamide (DMF). The suspension was heated to 90° C. and then stirred for 30 minutes. The resultant clear solution was cooled to 40° C., treated dropwise with 14 g of N,N-dimethylacetamide dimethyl acetal, and stirred for an additional 2.5 hours at 40° C. to 50° C. After the solvent was partially removed under vacuum, the mixture was then cooled to below 20° C. and treated with 14 ml of water. Acetic acid was then added to adjust the pH of the mixture to about 6.5. After the mixture was stirred for 30 minutes, its contents were analyzed by using HPLC. The results showed that the content of sucrose-6-acetate was 28.3% (85% yield).

EXAMPLE 2

Synthesis of sucrose-6-acetate

A four-neck, round-bottom flask with stirring apparatus was charged with 20 g of mashed sucrose, 50 ml of DMF, and 40 ml of pyridine. After the mixture was heated to 50° C., it was treated dropwise with 14 g of N,N-dimethylacetamide dimethyl acetal and then stirred for additional 4 hours at 40° C. to 50° C. After the solvent was partially removed under vacuum, the mixture was cooled to below 20° C. and treated with 9 ml of water. Acetic acid was then added to adjust the pH of the mixture to about 6.5. After the mixture was stirred for 30 minutes, its contents were analyzed by using HPLC. The results showed that the content of sucrose-6-acetate was 25.6% (77% yield).

EXAMPLE 3

Synthesis of sucrose-6-benzoate

A four-neck, round-bottom flask with stirring apparatus was charged with 20 g of sucrose and 90 ml of DMF. The suspension was heated to 90° C. and then stirred for 30 minutes. The resultant clear solution was cooled to 40° C., treated dropwise with 13 g of N,N-dimethylbenzamide dimethyl acetal, and stirred for additional 4.5 hours at 40° C. to 50° C. After the solvent was partially removed under vacuum, the mixture was cooled to below 20° C. and treated with 9 ml of water. Acetic acid was added to adjust the pH of the mixture to about 6.5. After the mixture was stirred for 30 minutes, its contents were analyzed by using HPLC. The results showed that the content of sucrose-6-benzoate was 30.5% (82% yield).

EXAMPLE 4

Synthesis of sucrose-6-acetate

A four-neck, round-bottom flask with stirring apparatus was charged with 34.2 g of sucrose and 140 ml of DMF. The suspension was heated to 90° C. and then stirred for 30 minutes. The resultant clear solution was cooled to 30° C., treated dropwise with 14 g of N,N-dimethylacetamide dimethyl acetal, and stirred for additional 3 hours at 30° C. to 40° C. After the solvent was partially removed under vacuum, the mixture was then cooled to below 20° C. and treated with 14 ml of water. Acidic ion exchange resin was added to adjust the pH of the mixture to about 6. After the mixture was stirred for 30 minutes, the reaction was stopped and the resin is removed by filtration. HPLC analysis showed that the content of sucrose-6-acetate in the mixture was 32%.

EXAMPLE 5

Synthesis of sucralose-6-acetate

Sucrose-6-acetate obtained from Example 1 was concentrated to form a syrup, to which 150 ml of DMF was added. After the mixture was cooled to below 0° C., 50 g of thionyl chloride was gradually added to the cooled mixture. The addition rate was carefully controlled to keep the temperature of the mixture below 30° C. After the addition was complete, the mixture was heated slowly to from 110° C. to 115° C. and maintained at this temperature for 3.5 hours. The mixture was then cooled to below 20° C. and neutralized by adding a sodium hydroxide aqueous solution. After most of DMF was evaporated under vacuum, 200 ml of water was added. The mixture was then extracted with ethyl acetate. The organic layers were combined and concentrated. Sucralose-6-acetate was crystallized from the concentrate and recrystallized to give a high-purity product.

EXAMPLE 6

Synthesis of sucralose

A mixture of 20 g of dry sucralose-6-acetate obtained from Example 5 and 70 ml of methanol was heated to from 40° C. to 50° C. When the reacting mixture became a clear solution, a small quantity of a 30% sodium methylate solution was added. After the mixture was stirred for 2 hours, methanol was removed under reduced pressure. The resultant mixture was diluted to a 30% mixture by adding a certain quantity of water, which was decolored and then filtered. The filtrate thus obtained was concentrated to a 65% solution, which was cooled to form crystallized sucralose. The obtained crystal was filtered and dried to give sucralose with a yield of over 95% and purity of over 98.0%.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method for preparing a sucrose-6-ester, comprising:
   (i) reacting sucrose with a N,N-dimethylcarboxamide dimethyl acetal in an inert aprotic solvent to form a cyclic acetal of formula (I):

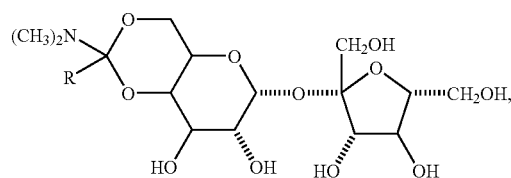

(I)

wherein R is $C_1$-$C_6$ alkyl, $C_3$-$C_{20}$ cycloalkyl, $C_1$-$C_{20}$ heterocycloalkyl, aryl, or heteroaryl; and (ii) subjecting the cyclic acetal to a mild acidic or substantially neutral hydrolysis to provide a sucrose-6-ester of formula (II):

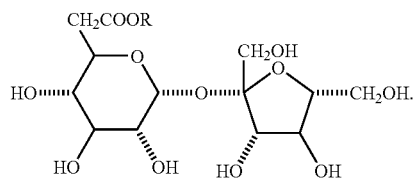

(II)

2. The method of claim 1, wherein R is methyl, ethyl, or phenyl.

3. The method of claim 1, wherein the N,N-dimethylcarboxamide dimethyl acetal is N,N-dimethylacetamide dimethyl acetal, N,N-dimethyl propionamide dimethyl acetal, or N,N-dimethylbenzamide dimethyl acetal.

4. The method of claim 1, wherein the amount of N,N-dimethylcarboxamide dimethyl acetal is within the range of from about 0.9 to about 2.0 molar equivalents to the amount of sucrose.

5. The method of claim 1, wherein the inert aprotic solvent is a member selected from the group consisting of N,N-dimethylformamide, dimethyl sulfoxide, N,N-dimethylacetamide, and pyridine.

6. The method of claim 1, wherein step (i) has a reaction temperature within the range of from about 20° C. to about 90° C.

7. The method of claim 1, wherein step (i) has a reaction time within the range of from about 2 hours to about 6 hours.

8. The method of claim 1, wherein the hydrolysis is carried out in a solution containing water, and the amount of water is within the range of from about 2 to about 10 molar equivalents of the amount of sucrose.

9. The method of claim 1, wherein the hydrolysis is carried out in the presence of an organic acid, an inorganic acid, or acidic ion exchange resin.

10. The method of claim 9, wherein the hydrolysis is carried out in the presence of acetic acid, formic acid, hydrochloric acid, or sulfuric acid.

11. The method of claim 9, wherein the hydrolysis is carried out at a pH within the range of from about 4 to about 7.

12. The method of claim 1, wherein the hydrolysis is carried out at a temperature not higher than about 20° C.

13. The method of claim 1, wherein the hydrolysis is carried out in a medium selected from the group consisting of an aqueous solution and a solution in organic solvent.

14. A compound of formula (I):

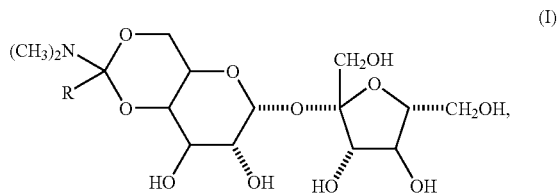

(I)

wherein R is $C_1$-$C_6$ alkyl, $C_3$-$C_{20}$ cycloalkyl, $C_1$-$C_{20}$ heterocycloalkyl, aryl, or heteroaryl.

15. The compound of claim 14, wherein R is methyl, ethyl, or phenyl.

16. A method for preparing sucralose, comprising:
   (i) reacting sucrose with a N,N-dimethylcarboxamide dimethyl acetal in an inert aprotic solvent to form a cyclic acetal of formula (I):

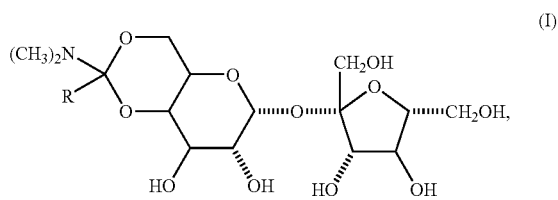

(I)

wherein R is $C_1$-$C_6$ alkyl, $C_3$-$C_{20}$ cycloalkyl, $C_1$-$C_{20}$ heterocycloalkyl, aryl, or heteroaryl;

(ii) subjecting the cyclic acetal to a mild acidic or neutral hydrolysis to provide a sucrose-6-ester of formula (II):

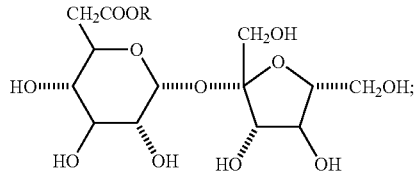
(II)

(iii) treating the sucrose-6-ester with a chlorinating agent capable of effecting selective chlorination at the 4-, 1'-, 6'-positions to form a sucralose-6-ester; and (iv) treating the sucralose-6-ester with a base to obtain sucralose.

17. The method of claim 16, wherein R is methyl, ethyl, or phenyl.

18. The method of claim 16, wherein the chlorinating agent is a Vilsmeier agent.

19. The method of claim 16, wherein the base is sodium methylate.

* * * * *

UNITED STATES PATENT AND TRADEMARK OFFICE
CERTIFICATE OF CORRECTION

PATENT NO. : 7,626,016 B2 Page 1 of 1
APPLICATION NO. : 11/841435
DATED : December 1, 2009
INVENTOR(S) : Jun Jing Wu It is certified that error appears in the above-identified patent and that said Letters Patent is hereby corrected as shown below:

<u>On the Title Pg Item (56) (Other Publications), Line 7</u>
Delete "Amidchloride" insert -- Amidochloride --.

<u>On the Title Pg Item (56) (Other Publications), Line 7</u>
Delete "(1960), ," insert -- (1960), --.

Signed and Sealed this

Nineteenth Day of January, 2010

David J. Kappos
*Director of the United States Patent and Trademark Office*